US009012136B2

(12) United States Patent
Delamarche et al.

(10) Patent No.: US 9,012,136 B2
(45) Date of Patent: *Apr. 21, 2015

(54) DETECTION OF AN ANALYTE IN A SAMPLE

(75) Inventors: Emmanuel Delamarche, Thalwil (CH); Daniel J. Solis, Encinitas, CA (US)

(73) Assignee: International Business Machines Corporation, Armonk, NY (US)

( * ) Notice: Subject to any disclaimer, the term of this patent is extended or adjusted under 35 U.S.C. 154(b) by 979 days.

This patent is subject to a terminal disclaimer.

(21) Appl. No.: 12/742,996

(22) PCT Filed: Oct. 30, 2008

(86) PCT No.: PCT/IB2008/054525
§ 371 (c)(1),
(2), (4) Date: May 14, 2010

(87) PCT Pub. No.: WO2009/069023
PCT Pub. Date: Jun. 4, 2009

(65) Prior Publication Data
US 2011/0117539 A1    May 19, 2011

(30) Foreign Application Priority Data
Nov. 29, 2007   (EP) ..................... 07121895

(51) Int. Cl.
| C12Q 1/00 | (2006.01) |
| C12Q 1/70 | (2006.01) |
| C12Q 1/68 | (2006.01) |
| G01N 33/53 | (2006.01) |
| A61K 49/00 | (2006.01) |
| G01N 33/543 | (2006.01) |
| G01N 33/536 | (2006.01) |
| B01L 3/00 | (2006.01) |

(52) U.S. Cl.
CPC ..... *B01L 3/502753* (2013.01); *B01L 3/502761* (2013.01); *B01L 3/5029* (2013.01); *B01L 2200/0668* (2013.01); *B01L 2300/0654* (2013.01); *B01L 2300/0681* (2013.01); *B01L 2400/0406* (2013.01); *B01L 2400/0688* (2013.01); *B01L 2400/086* (2013.01)

(58) Field of Classification Search
None
See application file for complete search history.

(56) References Cited

U.S. PATENT DOCUMENTS

| 5,723,345 | A | 3/1998 | Yamauchi et al. |
| 7,052,831 | B2 * | 5/2006 | Fletcher et al. ............... 435/5 |
| 7,695,687 | B2 * | 4/2010 | Delamarche et al. ......... 422/504 |
| 8,389,209 | B2 * | 3/2013 | Mertens et al. ............... 435/5 |
| 2003/0045001 | A1 | 3/2003 | Burgess et al. |
| 2003/0049833 | A1 | 3/2003 | Chen et al. |
| 2004/0259076 | A1 | 12/2004 | Farrow |
| 2006/0018797 | A1 | 1/2006 | Burnell et al. |
| 2007/0190641 | A1 | 8/2007 | Wilding et al. |
| 2007/0269893 | A1 | 11/2007 | Blankenstein et al. |
| 2008/0085551 | A1 | 4/2008 | Kim et al. |

FOREIGN PATENT DOCUMENTS

| JP | 07506256 A | 7/1995 |
| JP | 10506991 A | 7/1998 |
| JP | 2006138866 A | 6/2006 |
| JP | 2007519896 A | 7/2007 |
| KR | 100764022 B1 | 9/2007 |
| WO | WO 01/85341 A1 | 11/2001 |
| WO | WO 2009/069023 A3 | 6/2009 |

OTHER PUBLICATIONS

U.S. Appl. No. 13/459,764.
Office Communication—Notice of Non-Compliant Response to Restriction Requirement mailed on Oct. 11, 2012 for U.S. Appl. No. 13/459,764; 2 pages.
Response to Restriction Requirement filed Sep. 4, 2012, U.S. Appl. No. 13/459,764, 6 pages.
Restriction Requirement mailed on Aug. 6, 2012 for U.S. Appl. No. 13/459,764; 5 pages.

* cited by examiner

*Primary Examiner* — Benjamin P Blumel
(74) *Attorney, Agent, or Firm* — Stephen J. Walder, Jr.; Jennifer R. Davis

(57) ABSTRACT

There is provided mechanisms for the detection of an analyte in a sample. The mechanisms utilize at least a first measurement channel comprising a detection reactant corresponding to the analyte to be detected, and at least a microstructure associated with the first measurement channel. When the mechanisms are in use, the sample is introduced into the first measurement channel and propagated by way of the first measurement channel towards the microstructure. If the analyte is present in the sample, the analyte interacts with the detection reactant to form a networked product, and the microstructure is configured to filter the networked product.

11 Claims, 4 Drawing Sheets

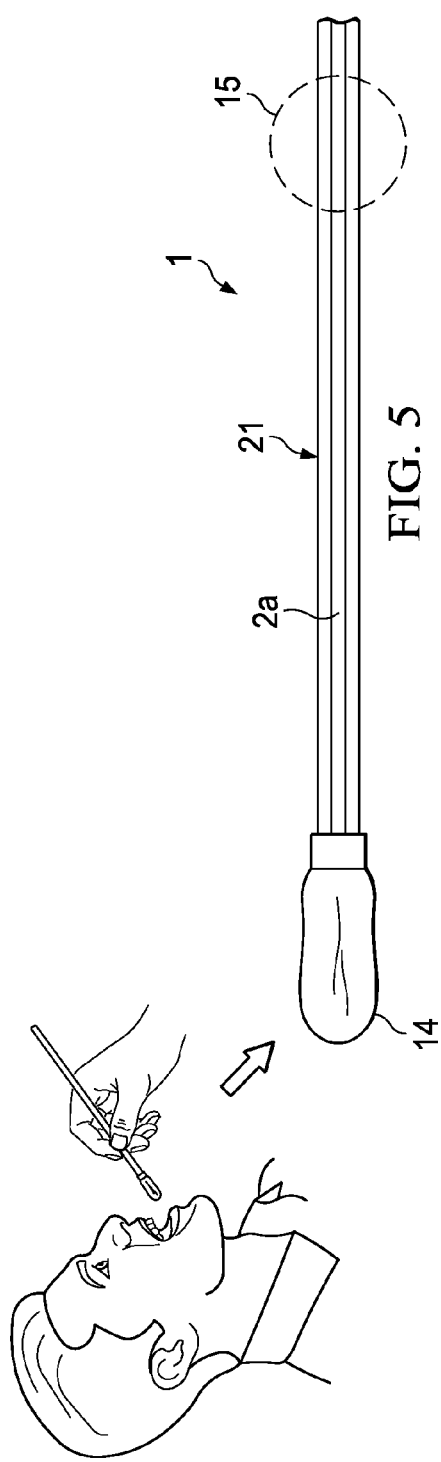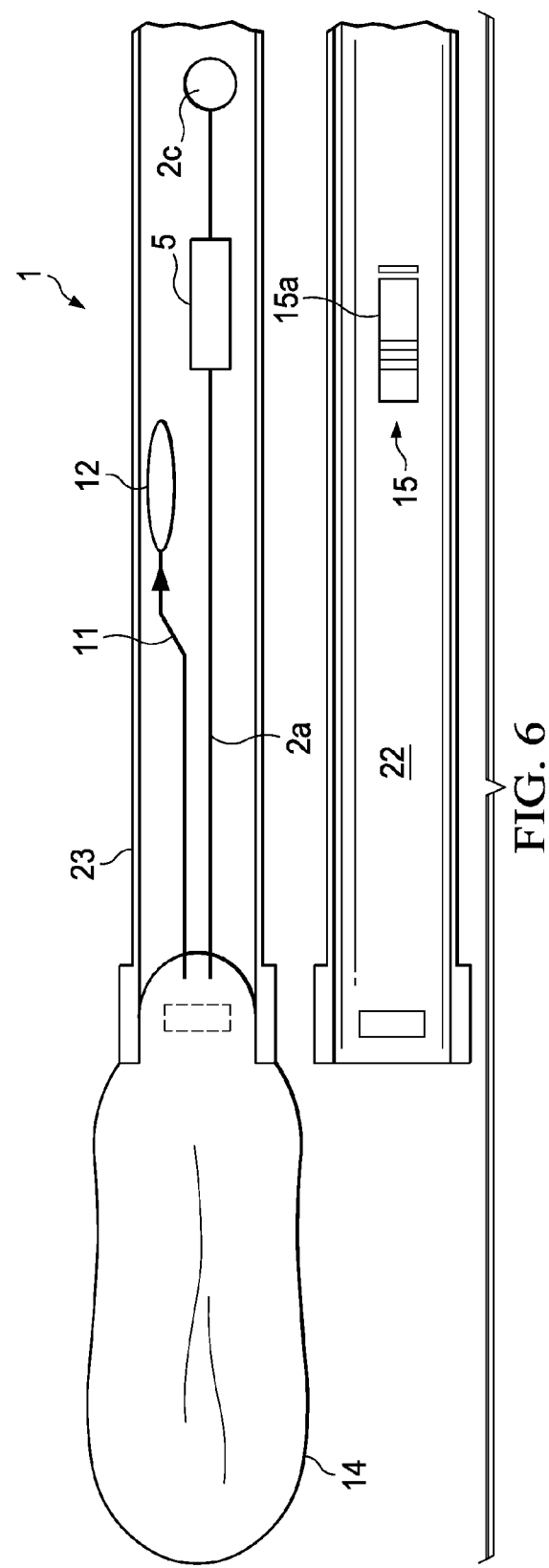

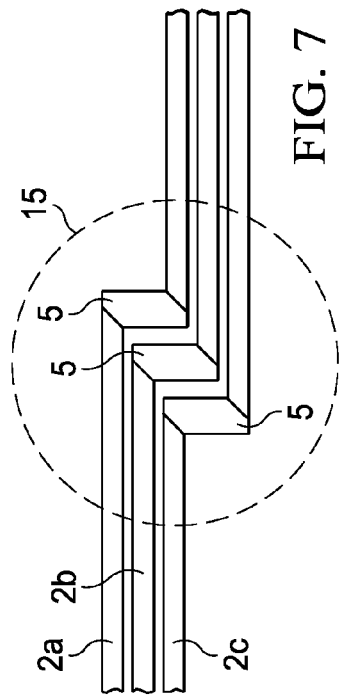
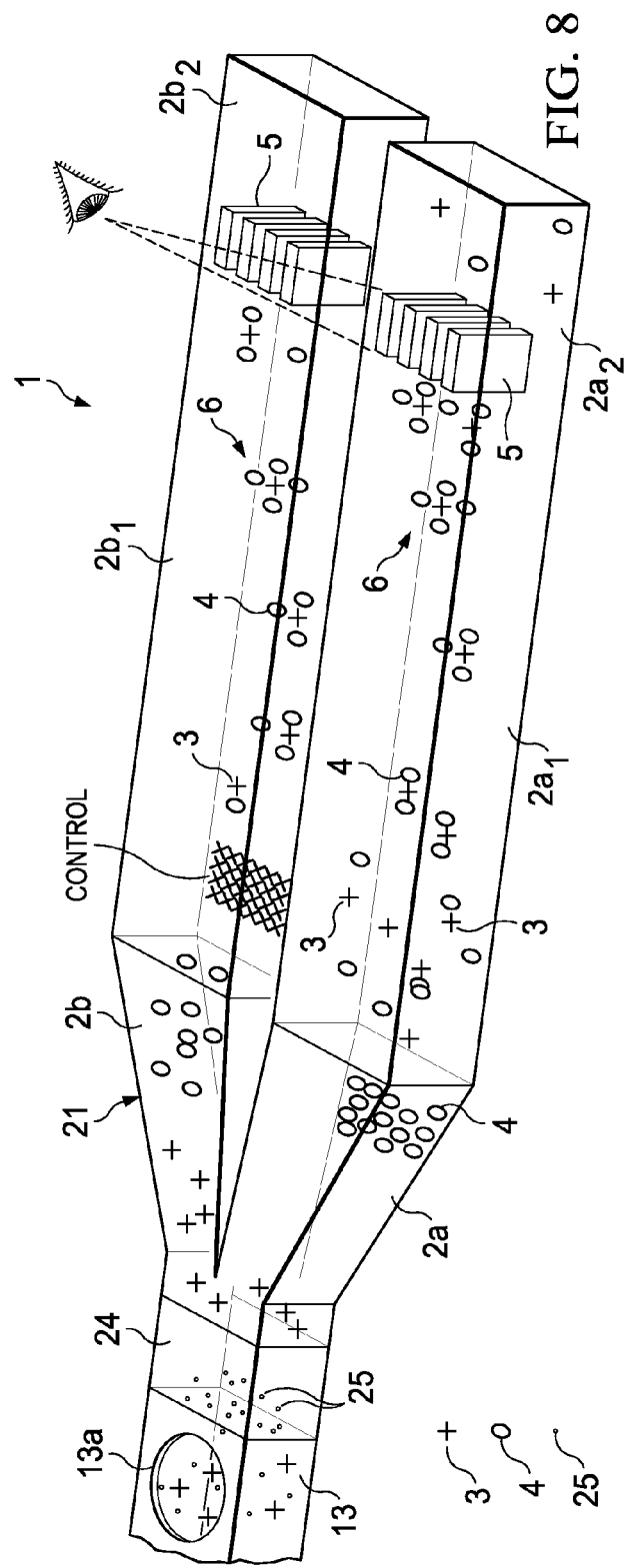

DETECTION OF AN ANALYTE IN A SAMPLE

BACKGROUND

The present invention relates to an apparatus and a method for detecting the presence of an analyte in a sample obtained from a person or animal. The present invention is applicable to the detection of different types of pathogens and particularly to the detection of an influenza virus.

Influenza is a disease that is caused in the animal species by the influenza virus. In humans, infection by the influenza virus may cause symptoms that are also common to less serious diseases such as the common cold and/or that are attributed to other diseases, such as, for example, gastroenteritis. Thus, infection with the influenza virus may be difficult to diagnose. If undiagnosed or wrongly diagnosed, influenza may lead to more serious health consequences, especially for certain age-groups, particularly the very young and the elderly, and/or for those suffering from other chronic medical conditions.

Influenza is transmittable from infected mammals via different media, for example, bodily fluids that are propagated via air by coughing or sneezing or contact with the blood or faeces of an infected person or animal via a contaminated surface.

Its contagious nature exacerbates the spread of influenza, which typically peaks during the winter months. When the influenza virus spreads rapidly in the human/animal population in a locality, this is referred to as an epidemic. When it spreads over a larger geographical area, for example, a country, a continent, or even across several continents, this is referred to as a pandemic. Controlling pandemics is a challenge since a virus strain found in a particular animal species, for example, birds, may mutate into a virulent form and spread amongst the population of that animal species if left uncontrolled and may kill large numbers of that population. The aforesaid mutated virus strain may cross-over into a second animal species, for example, humans, by interaction with a virus strain found in that second animal species to form an evolved version of the mutated virus strain, which can further mutate and cause a pandemic in the second animal species if not contained.

The types of known influenza virus types include: influenza virus A and its sub-types, influenza virus 8 and influenza virus C. It is the influenza virus A and its sub-types that are the most virulent and attributed to causing pandemics. The most recently identified sub-type of the influenza virus A, which potentially poses a pandemic threat is H5N1, more commonly known as the avian flu virus. Virus sub-types are also referred to as strains.

In order to reduce the spread of the influenza virus and/or the outbreak of a pandemic, infected persons should ideally be identified by the detection of the virus. If this is done early enough, for example, within 48 hours of infection, then the fatal consequences of the virus on an infected person may be reduced by the administration of appropriate drugs and, importantly, measures may be taken so that the infected person does not further spread the virus to others. Apart from also facilitating the surveillance of a virus outbreak, identification of an infected person may also assist in the development of a vaccine to reduce the spreading of the virus since vaccines contain inactivated forms of the most recently-detected influenza strain. Due to the mutative ability of viruses, it is typically the case that vaccines developed to contain a recent influenza outbreak may not be suitable for the same purpose for a subsequent influenza outbreak, for example, in the following year.

Some of the techniques that have been applied for influenza virus testing have been discussed herebelow.

Real-Time Polymerase Chain Reaction (RT-PCR)

In RT-PCR, a sample collected from the throat and/or nasopharynx of a person/animal is subjected to pre-treatment, thereby to further increase the solubility of mucus contained in the sample. The pre-treated sample is then processed so that a specific portion of the genome of a virus present in the sample, particularly, the deoxyribonucleic acid (DNA) or the ribonucleic acid (RNA), is amplified and rendered readable. The latter is done by using a complementary set of primers that is known to be associated to a specific section of the DNA/RNA of the virus that is being tested for.

RT-PCR is considered to be one of the techniques of choice for influenza virus testing on account of reliability and duration since it takes under 5 hours to obtain results. However, it has some associated disadvantages. Processing of the sample such as amplification of the DNA/RNA is specialized and done with the aid of peripheral equipment, which factors mean that such tests are done by skilled personnel and are expensive to perform. RT-PCR is a laboratory-based technique and may not be suitable for on-field testing, that is, on a site where infection by an influenza virus is considered to have occurred. Although it has recently been proposed to facilitate on-field detection by using a lab-on chip concept for RT-PCR, that is by incorporating all the components of the RT-PCR test on a common platform/substrate that can be transported to a site where testing is to be conducted, this may be expensive and testing can, again, only be performed by trained staff.

Agglutination Testing

This is a serological test which uses as its basis the fact that the influenza virus causes red blood cells to agglutinate or clump together. By subjecting a blood sample to a known antibody, the presence of a virus can be detected since the antibody would inhibit the agglutination of red blood cells by the virus. The agglutination inhibition can be observed by the sedimentation of red blood cells into the bottom of a conical test well to produce a distinct red dot. By respectively subjecting blood samples to increasingly diluted concentrations of the antibody, the sedimentation is seen to progressively decrease. The last dilution for which agglutination inhibition is detected provides information on the virus concentration in the host.

Like RT-PCR, agglutination testing can only be performed by trained staff and is done using specialized equipment and/or reagents. Furthermore, the cost and stability of reagents are an issue. This technique is primarily suited to being conducted in a laboratory; it would generally be considered to be unsuitable for on-field testing due to possible health and safety issues that could arise with open platforms. Due to the possible inconsistency in the way that the testing is conducted and/or interpretation of the results, agglutination testing may not be acceptable for surveillance of virus outbreaks. It is generally used for research and/or monitoring the health of individuals.

Tests Based on Immunoassays

Such testing is based on detecting viruses or antibodies produced in a host in response to infection by a virus by detecting antibody/antigen binding.

For antigen/antibody detection, immunofluorescence can be used. In this case, particles that are known to tag to specific antigens or antibodies and that fluoresce when illuminated with specific wavelengths of light are used. Although this technique can be used for detecting the presence of an influenza virus and for the further sub-typing of the influenza virus A, specialized microscopic techniques and/or reagents that are operable by skilled staff make this technique expensive, fragile and render it unsuitable for on-field virus testing.

There are some commercially available diagnostic tests for the detection of influenza viruses in a time-scale of between 10 to 30 minutes. They are based on lateral flow immunochromatography and are embodied in the form of strip-type detectors that provide a binary read-out on virus detection. Such tests may vary in the types of influenza viruses that are detectable and whether influenza types can be distinguished. Currently available tests are categorized based on the detection of: only influenza A viruses; both influenza A and B viruses, but no distinction can be made between the two types, or both influenza A and B and distinction can be made between the two. Currently, such diagnostic testing kits are unable to provide information on influenza A subtypes, which are attributed with causing/potentially causing pandemics. Furthermore, there is inconsistency in the sample specimens that are used for such tests, for example, some may use throat, nasopharyngeal, or nasal aspirates whilst others may use swabs, or washes. The specificity and, in particular, the sensitivity of such tests are lower than for viral culture and variable according to the particular test. Although the results of such tests may be obtained on a much shorter time-scale compared to other known techniques for influenza testing, a trade-off exists with respect to the sensitivity. Due to the lower sensitivity, negative test results may need to be confirmed by viral cultures or other methods such as agglutination testing or RT-PCR in order to flag whether they are false-negative results, especially during periods of peak community influenza activity. In contrast, false-positive rapid test results are less likely, but can occur during periods of low influenza activity.

U.S. Pat. No. 5,723,345 discloses a method of determining the amount of a substance in a liquid sample comprising: flowing a signal substance generator and a liquid sample through a predetermined channel in a predetermined direction, such that a specific binding reaction takes place with at least the substance and the signal substance generator, thereby causing the formation of a specific distribution of the signal substance generator in the channel, which is dependent on the concentration of the substance, the specific distribution formed by an affinity chromatographic, or an immunoprecipitation process; generating a signal substance from the signal substance generator specifically distributed in the channel; allowing dispersion of unreacted signal substance generator throughout the channel; allowing diffusion of the signal substance to a plurality of detection means arranged in different positions in the flow direction, detecting the signal substance with the plurality of detection means, and determining the concentration of the substance from the relative signal detected at the detection means. In this method, several different types of reagents and chemicals are used, which may increase the cost of producing such devices. Further, signal acquisition devices and signal-processing using mathematical models may serve to increase the complexity of operating this device. This requires adding functionality to the device, which increases its cost of fabrication and may serve to reduce the overall reliability, stability, and shelf lifetime of the device.

US-A1-2003/0045001 discloses an immunochromatographic test strip having a curved sample application zone, which functions similarly to standard immunochromatographic test strips but has a different sample collection zone. This method may ease the collection of some kinds of samples, such as, for example, blood taken from a finger, but may not be suitable for loading typical samples for detecting influenza viruses and other pathogens onto a test strip. Being based on a similar principle to immunochromatographic strip testing, the present technique may also suffer from the same drawbacks.

Accordingly, it is desirable to provide a technique for the detection of an influenza virus that mitigates and/or obviates the drawbacks associated to known techniques for the same purpose.

SUMMARY

In one illustrative embodiment, an apparatus for the detection of an analyte in a sample is provided. The apparatus comprises at least a first measurement channel comprising a detection reactant corresponding to the analyte to be detected. The apparatus further comprises at least a microstructure associated with the first measurement channel. When the apparatus is in use, the sample is introduced into the first measurement channel and propagated by way of the first measurement channel towards the microstructure such that the analyte, if it is present in the sample, interacts with the detection reactant to form a networked product. The microstructure is configured to filter the networked product.

In another illustrative embodiment, a method for the detection of an analyte in a sample is provided. The method comprises providing at least a first measurement channel comprising a detection reactant corresponding to the analyte to be detected, and at least a microstructure that is associated with the first measurement channel. The sample is propagated by way of the first measurement channel towards the microstructure such that the analyte, if it is present in the sample, interacts with the detection reactant to form a networked product. The microstructure filters the networked product.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

Reference will now be made, by way of example, to the accompanying drawings in which:

FIG. 5 shows a further illustrative embodiment of the present invention;

FIG. 6 refers to the illustrative embodiment in FIG. 5 and schematically shows such apparatus with a detached cover;

FIG. 7 shows a viewing zone according to an illustrative embodiment of the present invention; and FIG. 8 shows a further illustrative embodiment of the present invention.

DETAILED DESCRIPTION

Figure 1:
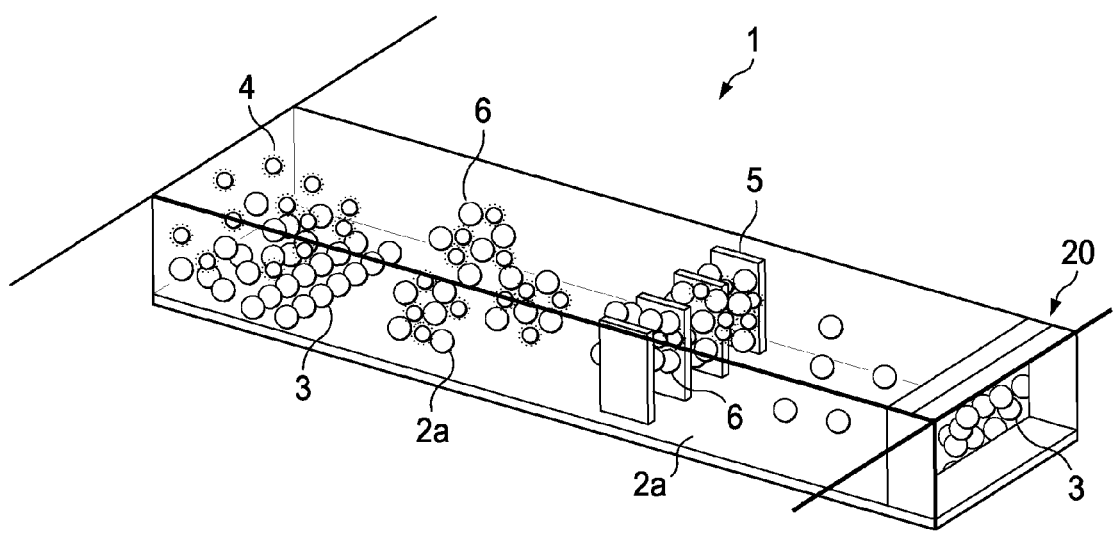
FIG. 1 schematically illustrates an illustrative embodiment of the present invention.

According to a first aspect of the present invention, there is provided an apparatus for the detection of an analyte in a sample. The apparatus comprises at least a first measurement channel comprising a detection reactant corresponding to the analyte to be detected, and at least a microstructure associated with the first measurement channel. When the apparatus is in use, the sample is introduced into the first measurement channel and propagated by way of the first measurement channel towards the microstructure such that the analyte, if it is present in the sample, interacts with the detection reactant to form a networked product, and the microstructure is configured to filter the networked product.

For the formation of the networked product, only a single receptor that is known to be a natural target of the analyte, i.e. with which the analyte is known to react and bind with to form an agglutination-type product, need be chosen as a part of the detection reactant in an embodiment of the present invention. Like the so-called strip tests, such as immunochromatographic tests, identification of an analyte in a sample may be done without the need for and/or specialised knowledge of specialised processing techniques and/or equipment. Thus, an illustrative embodiment of the present invention combines the advantageous features of agglutination-based tests and strip-tests. Some further advantageous features provided by an illustrative embodiment of the present invention include: (1) by virtue of choosing an appropriate detection reactant, any analyte that it is desired to confirm the presence of in a sample, may be identified; (2) the presence of more than one analyte in a sample may be confirmed by, for example, incorporating a corresponding number of measurement channels each comprising a different detection reactant that is chosen in accordance with an analyte to be identified; and (3) the form factor of an embodiment of the present invention may be designed to be comparable to strip-test devices and so provides ease of use and versatility of operation. These features are particularly advantageous to reduce the spreading of contagious viruses since, for example, both the testing and confirmation of a virus outbreak may be done on-site where, by contrast, with other techniques, only the sample collection would be done on-site and further testing to confirm the presence of the virus would be performed off-site usually in a laboratory.

In some illustrative embodiments, the networked product provides an optically-readable signal. In this way, the presence of a given analyte in a sample may be confirmed with ease and in an uncomplicated manner.

In one illustrative embodiment, an indicator is provided that is configured to indicate the filtering of the networked product by the microstructure. In this way, a further confirmation of the presence of the analyte in the sample may be obtained.

In some illustrative embodiments, at least a second measurement channel is provided with at least an associated microstructure. By incorporating another measurement channel, further knowledge on the sample and/or detected analyte may be obtained.

The second measurement channel may be configured to differ from the first measurement channel in that it has at least a different associated hydrodynamic and/or chemical property. By way of the difference in hydrodynamic properties, different levels of sensitivity may be incorporated in an embodiment of the present invention. By way of the difference in chemical properties of the measurement channels, the performance of an embodiment of the present invention may be further improved since such properties may be chosen so as to increase the probability of interaction between the sample and the detection reactant and decrease the probability of, for example, clogging of the measurement channels.

In some illustrative embodiments, the second measurement channel is configured to differ from the first measurement channel such that the networked product is formed with a different characteristic. By way of example, in an embodiment of the present invention, the second measurement channel may be configured to comprise the same detection reactant as that in the first measurement channel. Thus, they will detect the same analyte, if it is present in the sample.

By configuring the second measurement channel such that the networked product is formed with a different formation characteristic compared to that in the first measurement channel, the concentration of the analyte may be determined. In this regard and for the sake of example, the formation characteristic may be chosen to be the length of the measurement channel. In this regard, the second measurement channel may be configured such that the interaction of the sample with the detection reactant to form the networked product and the collection of the networked product by the microstructure associated with the second measurement channel occurs over a shorter length than in the first measurement channel. For substantially the same characteristics being possessed by the microstructures associated with the first and second measurement channels, the concentration of the networked product collected by the microstructure associated with the second measurement channel will be necessarily higher than that collected at the first measurement channel.

Obtaining knowledge on the concentration of the analyte in a sample may be advantageously applied to determine the treatment to be administered to a person. Furthermore, by applying an embodiment of the present invention to determine the concentration of an analyte periodically, monitoring the effect of administered drugs, incubation period of viruses, for example, may be done.

In some illustrative embodiments, the second measurement channel may be configured to differ from the first measurement channel in that it comprises a different detection reactant. This feature provides the advantage that an embodiment of the present invention may be configured to detect different analytes present in the same sample simultaneously.

In some illustrative embodiments, the measurement channel comprises a microfluidic capillary. An advantage associated with implementing the measurement channel with a microfluidic capillary is that, in contrast to nitro-cellulose-based, immunochromatographic membranes, the capillary action by way of which the sample is propagated along the length of the capillary is controllable. In this way, the uniformity with which the sample and the reagents in the measurement channel, including the detection reactant, interact with each other may be increased. A further advantage associated with this feature is that the problems encountered with the clogging of immunochromatographic membranes by agglutination products such as the networked product may be avoided.

The microfluidic capillary may be designed such that the formation of the networked product is controllable. It is desirable to control the formation of the networked product in order to improve its detection when collected at the microstructure. In an illustrative embodiment, this is achieved by matching a physical dimension of the microfluidic capillary to the chemical pathway of the reaction by way of which the networked product is formed. Examples include: matching the length of the capillary to the time estimated for the formation of the networked product or matching the depth of the capillary to increase/decrease the diffusion of reagents, such as, for example, the detection reactant in the capillary. Thus, and in contrast to immunochromatographic membranes, the flow control and the geometry of the microfluidic capillary may be chosen to tailor the kinetics of the formation of the networked product as desired.

In some illustrative embodiments, the measurement channel is configured to comprise at least a cavity for the storage of the detection reactant. Preferably, the cavity is formed during the fabrication of an embodiment of the present invention and the detection reactant may be incorporated in the cavity at this stage in powder form or by being dried onto the surface of the cavity. In both cases, introduction of the sample, which would typically be in fluid form, in the measurement channel would cause the detection reactant to dissolve.

In some illustrative embodiments of the present invention a viewing zone is provided from where the filtered networked product is visually detectable. A given measurement channel in an illustrative embodiment of the present invention may be a microfluidic capillary and has dimensions on the micronscale. Thus, this may pose a challenge to visually detect the filtered networked product. In order to alleviate this problem, a viewing zone is provided in illustrative embodiments of the present invention, which is configured to enhance the visual detection of the filtered networked product. In one illustrative embodiment, the viewing zone is a window provided above the region where a microstructure corresponding to the first and/or second measurement channel is coupled thereto. In one illustrative embodiment, the window comprises a material that is substantially transparent and/or that comprises a magnifier.

At least one of the first and second measurement channels may be configured to have a predefined geometrical shape substantially in a region where it is coupled to the microstructure corresponding thereto. The visual detection of the networked product collected in the microstructure coupled to a given measurement channel is dependent on the concentration of the networked product that is formed. In order to compensate for the reduced visibility of the networked product collected by the microstructure, if it is formed with a reduced concentration, the measurement channel may be designed to have a predefined geometrical shape in the region where it is coupled to its associated microstructure. In this regard, and in one illustrative embodiment, the geometrical shape is chosen so as to enhance the visual detection of the networked product collected by the microstructure. For example, the measurement channel may incorporate a step where it is coupled to its associated microstructure. This feature may also be applied in incorporating the desired number of measurement channels without the need to change the form factor of the illustrative embodiment. For example, fewer but wider measurement channels may be implemented or, alternatively, more but narrower-width measurement channels may be incorporated in an illustrative embodiment, which would both serve to enhance the visual detection of the networked product collected in the microstructures associated with the measurement channels.

In some illustrative embodiments. a sample control channel is provided that is configured to test for the cross-reactivity of the sample. By testing for the cross-reactivity of the sample, it may be determined if it comprises a chemical that may interfere with and/or prevent the formation of the networked product. In this way, the reliability of the illustrative embodiments may be further improved. This feature provides the further advantage that the presence of an artefact of a vaccine corresponding to the analyte that the sample is being tested for may also be determined, thus preventing the scenario that a person/animal receives multiple vaccination treatments against the same analyte. A further advantage is also that a first-time infected person/animal may be delimited from one that has received vaccination treatment for combating infection by a specific analyte.

In some illustrative embodiments, a test control channel and/or an area configured to monitor testing for a given analyte is provided. In order to determine whether an embodiment of the present invention may be reliably applied for testing for a given analyte, a test control channel is provided. The test control channel is configured to comprise, for example, the analyte to be tested for and a corresponding detection reactant. It is furthermore configured such that, when a sample to be tested is flowed in the test control channel, the analyte and the detection reactant interact, thereby forming a networked product. In other words, if there are no abnormalities in the performance of the illustrative embodiment, the networked product should form in the test control channel whether or not the analyte is actually present in the sample that is being tested. Such abnormalities may include, for example, that an illustrative embodiment of the present invention has exceeded its shelf-lifetime, malfunctioning reagents due to, for example, storage or exposure of an illustrative embodiment of the present invention at excessive temperatures that may damage the reagents, the dynamics of the interaction between the sample and reagents not being as they should be due to a fabrication problem whereby sealing of the device or positioning of the reagents was not properly effected, or the like.

In some illustrative embodiments, a sample collection channel is provided that is configured to be unidirectionally coupled to a sample storage unit. In this case, excess sample may be channelled into the sample collection channel and then directed to a sample storage unit where it is stored. The sample collection channel is configured such that the flow of the sample is unidirectional, i.e. in the direction of the sample storage unit, and unable to revert on its flow path.

In some illustrative embodiments, a sample collection unit is provided that is configured for the collection of the sample to be tested. A sample to be tested for the presence of a particular analyte is collected from a person/animal via a sample collection unit, which is then appended to one or more of the measurement channels in illustrative embodiments of the present invention.

The sample collection unit may further comprise at least a sample processing unit. By way of this feature, pre-processing of the sample may be done, for example, to alter its physical properties thereby to improve the performance of an embodiment of the present invention in the detection of a given analyte. Such physical properties may include pH, viscosity, transparency, stability and ionic-strength, for example.

The sample collection unit may comprise at least one filter. By incorporating at least one filter in the sample collection unit, it becomes possible to reduce the probability of mucus, tissue fragments, cells, etc present in the sample collected from a person/animal to be tested from entering and/or clogging the flow path of the sample in the measurement channel. In this way, the performance of an illustrative embodiment of the present invention may be further improved.

The sample collection unit may comprise a swab. This feature provides the advantage of ease of collection of a sample from a person/animal to be tested. To further improve the performance of an illustrative embodiment of the present invention, the swab may be prepared with chemicals added thereto so that processing of the sample can be initialised. The swab may be substantially saturated with the sample taken from a person to be tested in order that the test does not have to be repeated due to the absence of enough sample to perform the test on, for example. In an illustrative embodiment of the present invention, the swab may be configured to indicate, such as by way of a colour change, for example, whether it is substantially saturated or not by the sample.

A filtration power of the microstructure associated with at least one of the first and second measurement channels may be configured according to an estimated size, shape, at least one chemical property or a combination thereof of the networked product. By tailoring the filtration power of the microstructure in accordance with one or more known properties of the networked product, the performance of an illustrative embodiment of the present invention may be further improved since the probability of retaining the networked product in the microstructure and, therefore, detecting it, is further increased.

In some illustrative embodiments, a further microstructure may be provided, that is associated with at least one of the first and second measurement channels, and which is configured to have a different filtration power from the microstructure associated with the same measurement channel. In this way, the analyte concentration in the sample and/or the extent of the formation of the networked product in the measurement channel may be deduced.

The detection reactant may comprise an optically-detectable material. In this way, a macroscopic indication of the formation of the networked product and, therefore, the presence of an analyte in the sample, may be obtained.

The detection reactant may be adapted to be chemically linked to at least one receptor that can specifically bind to the analyte. In this way, the presence of a given analyte in a sample may be confirmed with ease and in an uncomplicated manner.

At least one of the first and second measurement channels may be configured to further comprise at least an inhibitor. In an illustrative embodiment of the present invention, the choice of inhibitor may be made for different purposes. For example, the inhibitor may be chosen on account of possessing the property that it may be applied in controlling the size of the networked product. In this way, clogging of the measurement channel may be reduced. Alternatively, the inhibitor may be chosen to reduce the probability of coagulation of the dye-particles, thus improving the performance of an illustrative embodiment of the present invention. As a further alternative, the inhibitor may be chosen on account of possessing the property that it inhibits the interaction of known analytes with the detection reactant provided in any one of the measurement channels of an embodiment of the present invention. In this way, the probability of at least identifying the presence of a previously-unknown analyte may be increased.

In some illustrative embodiments, at least one of the first and second measurement channels may be configured to further comprise at least an intermediate reagent for interaction with the analyte. The intermediate reagent is chosen on account of being able to interact with the analyte in such a way so as to amplify the number of binding sites on the analyte by way of which it can interact with the detection reactant for the formation of the networked product. In this way, the detection of an analyte in a sample may be further improved.

The analyte may comprise a pathogen. The illustrative embodiments are not restricted to the detection of a particular analyte but may be generally applied to the detection of different pathogens, for example, viruses and their sub-types, bacteria, etc., or other types of analytes. This feature offers the advantage of versatility.

In some illustrative embodiments, the analyte comprises an influenza virus and, particularly, the influenza virus A.

Corresponding method aspects are also provided wherein, according to illustrate embodiments of the present invention, there is provided a method for the detection of an analyte in a sample comprising the steps of: (1) providing at least a first measurement channel comprising a detection reactant corresponding to the analyte to be detected; and (2) providing at least a microstructure that is associated with the first measurement channel. The method illustrative embodiments may further comprise the steps of: (1) propagating the sample by way of the first measurement channel towards the microstructure such that the analyte, if it is present in the sample, interacts with the detection reactant to form a networked product; and (2) filtering the networked product by way of the microstructure.

Any disclosed illustrative embodiment may be combined with one or several of the other illustrative embodiments shown and/or described. This is also possible for one or more features of the illustrative embodiments. Any feature of one aspect of the invention may be applied to another aspect of the invention and vice versa.

With reference now to the figures, the same reference numbers or signs are used to denote the same parts or the like. FIG. 1 is a schematic illustration of an illustrative embodiment of the present invention.

As can be seen from FIG. 1, an embodiment of the present invention comprises an apparatus 1 comprising at least a first measurement channel 2a. In the first measurement channel 2a, there is provided a detection reactant 3 corresponding to the analyte 4 whose presence in the sample is to be confirmed. Furthermore, there is also provided a microstructure 5 that is associated with and coupled to the first measurement channel 2a. When the apparatus 1 is in use, a sample that is to be tested for the presence of the analyte 4 is introduced into the first measurement channel 2a and propagated by way of the first measurement channel 2a towards the microstructure 5 such that the analyte 4, if it is present in the sample, interacts with the detection reactant 3 to form a networked product 6. The microstructure 5 is configured to filter the networked product 6, thereby to provide an indication of the presence of the analyte 4 in the sample. In this context, filtering preferably means that networked products 6 will be captured by the microstructure 5 while unreacted particles overcome the microstructure 5. In an example, the networked products 6 may typically show an effective size of >500 nm each such that the microstructure forms a barrier for particles of that size. Unreacted particles—be it detection reactant particles 4 or other particles—may pass the microstructure 5, move further down the measurement channel 2a, and will be captured in a control area 20. Provided a networked product 6 cannot be detected at the mircostructure 5 the control area 20 helps a user to distinguish between a real negative test result and a failure in the apparatus. A scenario in which particles, especially detection reactants 3, can be detected in the control area 20 after a test was conducted provides an indication if not a proof that the measurement channel including the microfluidic capillary works and that the microstructure 5 does not generally inhibit particles from passing. This information can help to determine that there was no analyte present in the sample. If, on the other hand, the control area 20 does not show any particles or detection reactants 3 then the measurement channel does not work as otherwise some particles should have moved down the measurement channel 2a, passed the microstructure 5, and piled up in the control area 20.

In order to facilitate ease of confirmation of the analyte 4 in a sample being subjected to testing, in an embodiment of the present invention, the networked product 6 provides an optically-readable signal, for example, it inherently has optically-detectable properties. In order that the networked product 6 has the capability of providing an optically-readable signal, in an embodiment of the present invention, the detection reactant 3 is chosen to comprise an optically-detectable material. In this regard, its optical properties may be inherent or a result of the interaction of the detection reactant 3 with the analyte 4, if it is present in a sample being tested. In one illustrative embodiment, for the detection reactant 3, dye particles having a diameter of a few micrometres are chosen. By using dye particles, the problems associated with photobleaching and sedimentation may be avoided. By virtue of the diameter dimensions, collection of the networked product 6 at the microstructure 5 is not dominated by the time taken for the formation of the networked product 6 and/or distance over which it is formed. Furthermore, corresponding dimensions of the microstructure 5 may be chosen, which reduces the costs associated with the fabrication of the microstructure 5 since techniques such as plastic moulding or hot embossing may be used for this purpose. In an embodiment of the present invention, the detection reactant 3 comprises polystyrene beads containing a dye.

In order to provide further confirmation of the presence of a given analyte 4 in a sample, an illustrative embodiment of the present invention may be configured to comprise an indicator (not shown) configured to indicate the filtering of the networked product 6 by the microstructure 5. An illustrative embodiment of the present invention may be configured such that the collection of the networked product 6 in the filter microstructure 5 triggers a change in an indicator, thereby to signal the presence of the analyte 4 in the sample. The indicator may, for example, be a strip placed after the microstructure 5 where the networked product 6 is collected. The indicator could be configured such that collection of the networked product 6 in the filter microstructure 5 causes a change in a physical property of the indicator. Whether or not a change in the physical property has occurred is monitored and provides a binary-readout signal as to the absence/presence of the analyte 4 in the sample. In this case, the physical property may be chosen to be, for example, electrical, optical, chemical or a combination thereof. Of course, the present invention is not limited to the choice of stated physical properties and any other appropriate property may be chosen for this purpose.

The first measurement channel 2a is implemented with a microfluidic capillary in an embodiment of the present invention. Several features may be incorporated into the microfluidic capillary to further improve the performance of illustrative embodiments of the present invention. For example, the microfluidic capillary may be fabricated to comprise a cavity (not shown). The cavity may, for example, be applied for the storage of the detection reactant 3, which is incorporated in the cavity in powder form or by being dried onto the surface of the cavity. In both cases, introduction of the sample, which would typically be in fluid form, in the first measurement channel 2a would cause the detection reactant 3 to dissolve and interact with the analyte 4. By incorporating the detection reactant 3 during the fabrication stage of the microfluidic capillary, any complications that may arise from its introduction at a later stage, for example when the sample is introduced into the first measurement channel 2a, may be avoided. An example of such complications includes the coagulation of the detection reactant 3 with debris in the sample, which may hinder the detection of an analyte 4 in the sample.

In order to improve the interaction of the analyte 4, if it is present in a sample subjected to testing in accordance with an illustrative embodiment of the present invention, with a corresponding detection reactant 3, the detection reactant 3 is adapted to be chemically linked to at least one receptor that can specifically bind to the analyte 4. In this regard, the detection reactant 3 may be chosen so as to comprise dye-particles whose surface is functionalized with a type of receptor that is known to interact and bind to the analyte 4 to be detected in the sample to form a networked product 6. Further details on the types of receptors that may be used in illustrative embodiments of the present invention applied for the detection of influenza viruses will be given herebelow.

The apparatus 1 can be applied for the detection of a variety of different analytes 4, including different types of pathogens such as, for example, viruses and bacteria. By way of example, the application of the apparatus 1 for the detection of the influenza virus will be generally described hereinafter.

It is known that influenza viruses bind to sugars present on the surface of cells. It is also known that influenza viruses can be distinguished by specific sialic acid terminal residues displayed on glycan receptors, for example. In combination, this information is advantageously applied in illustrative embodiments of the present invention for the detection of influenza viruses present in a sample. Specifically, and as can be seen from FIG. 2, in some illustrative embodiments of the present invention, the surfaces of particles of the detection reactant 3 are functionalized with a glycan receptor 7. By way of a cross-linker 8, the glycan receptor 7 may be adapted to display a specific sialic acid terminal residue 9, which corresponds to an influenza virus that it is desired to be detected.

Figure 2:
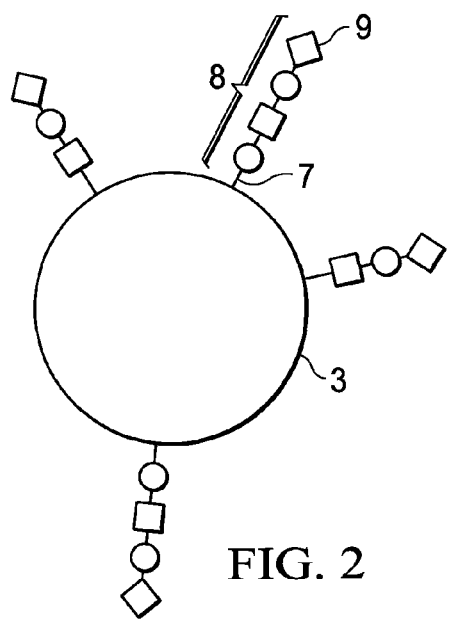
FIG. 2 schematically illustrates a particle of the detection reactant in an illustrative embodiment of the present invention whose surface is functionalized with a receptor.
Figure 3:
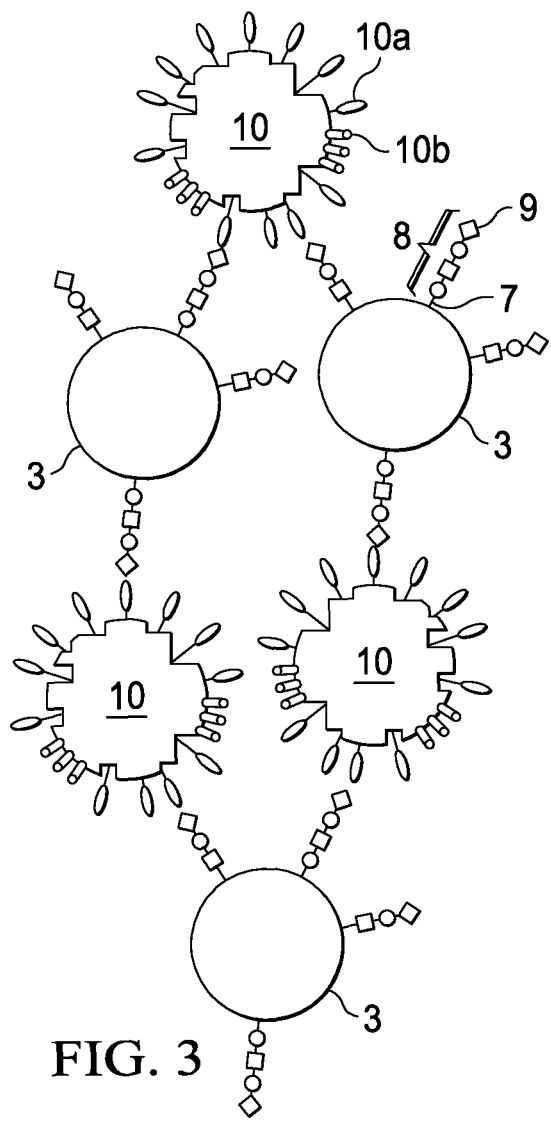
FIG. 3 schematically illustrates the interaction between an influenza virus and particles of the detection reactant modified as shown in FIG. 2.

Reference is now made to FIG. 3, which schematically illustrates how an influenza virus 10 present in a sample being tested in accordance with some illustrative embodiments of the present invention would interact with the detection reactant 3 whose surface has been modified as described with reference to FIG. 2. As can be seen from FIG. 3, the influenza virus 10 has an associated hemagglutinin (HA) component 10a and neurimidase (N) component 10b. It is the hemagglutinin component 10a that binds with the sialic acid terminal residue 9 of the detection reactant particles. Based on this bonding and the properties of the carbohydrate structure of the receptor, different types and strains of influenza viruses may be detected with illustrative embodiments of the present invention. For example, avian influenza HA bind with alpha 2-3 sialic acid receptors while human influenza HA bind with alpha 2-6 sialic acid receptors. Thus, a specific glycan can be applied for detecting a specific type of influenza virus.

In some illustrative embodiments of the present invention, different types of receptors may be used for modifying the surfaces of particles of the detection reactant 3 such as, for example, antibodies, phage-displayed molecules or redblood cells, for example. In one illustrative embodiment, glycan receptors are used on account of their increased stability compared to, for example, antibody receptors. Furthermore, research on glycan arrays continuously updates the knowledge that is available on the different types of viruses and what types of receptors they bind to and this may be used advantageously in some illustrative embodiments of the present invention. Furthermore, since the infection by influenza viruses is mediated by binding of the virus to glycans on host cells, an illustrative embodiment of the present invention may be advantageously applied for the detection of new and infectious virus strains.

Regarding the microstructure 5 associated with, and coupled to, the first measurement channel 2a, the microstructure 5 may be configured according to an estimated size, shape, at least one chemical property, or a combination thereof, of the networked product 6. By tailoring the filtration power of the microstructure 5 in accordance with one or more known properties of the networked product 6, the performance of the illustrative embodiments of the present invention may be further improved since the probability of retaining the networked product in the microstructure and, therefore, detecting it, is further increased.

Figure 4:
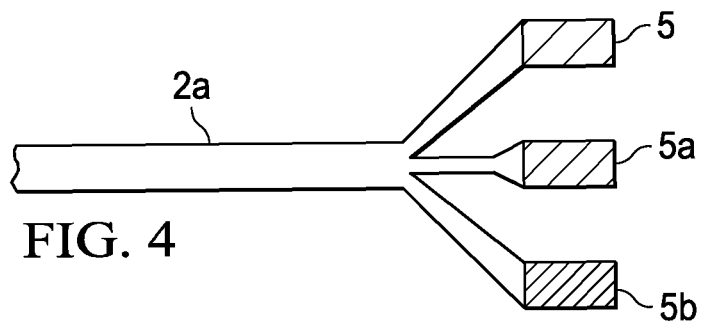
FIG. 4 schematically illustrates an illustrative embodiment of the present invention in which a plurality of microstructures are incorporated for use with a measurement channel.

The illustrative embodiments of the present invention are not limited to the use of one microstructure 5 with the first measurement channel 2*a*. To the contrary, further microstructures may be incorporated for use with the first measurement channel 2*a*. This is schematically illustrated in FIG. 4. In this regard, the different microstructures 5, 5*a*, 5*b* are configured to have a different filtration power from each other. By, for example, the gradation of the filtration powers of the microstructures, whereby one of them has a higher/lower filtration power than the other (e.g., filtration power of microstructure 5*b*>filtration power of microstructure 5*a*>filtration power of microstructure 5), the analyte concentration in the sample and/or the extent of the formation of the networked product in the measurement channel may be deduced.

With reference to FIG. 8, another illustrative embodiment of an apparatus 1 is shown. The apparatus 1 in this other illustrative embodiment comprises two measurement channels 2*a* and 2*b* in a housing 21. The measurement channels 2*a*, 2*b* comprise different sections/units as follows: a common sample collection unit 13, a common sample processing unit 24, channel sections 2*a*1, 2*b*1, and connecting channels 2*a*2, 2*b*2. In the following, if features of the two-channel embodiment are disclosed it is understood that such features are also regarded as disclosed for illustrative embodiments comprising only one measurement channel unless such feature inherently needs a two-channel configuration as a basis.

An opening 13*a* in the upper part of the housing 21 in the sample collection unit 13 allows the initial loading of a sample aliquot. The opening 13*a* is , in one illustrative embodiment, approximately 8 mm in diameter. This size permits the easy loading of a sample by hand using a pipette, a swab or a micropipette without requiring too large of a footprint on the device. In one illustrative embodiment, the sample collection unit 13 may be a cavity which is approximately several mm long with a height of approximately 6 mm thereby allowing a few ten to a few hundred microliters of sample to be accommodated. The sample collection unit 13 is connected to a sample processing unit 24 inside which a material or structures are defined to filter particulates and cells from the sample. The material can be glass fibers, a filter paper or, membrane with pores larger than 1 or a few micrometers, or the like, for example. The cavity represented by the sample processing unit 24 preferably can contain up to approximately 100 microliters of sample.

The sample processing unit 24 is connected to channel sections 2*a*1 and 2*b*1. In one illustrative embodiment, each channel section 2*a*1, 2*b*1 is approximately 400 micrometers wide, approximately 50 micrometer deep, and approximately 30 mm long and has a total volume of approximately 0.6 microliter. A channel section having such dimensions has a low hydraulic resistance and is not too large thereby preventing an inhomogeneous filling front of liquid to occur due to gravity.

Detection reactants 3 for forming the networked product 6, can be chemicals, enzymes, proteins, salts, and other agents which may be deposited in the first half of the channel sections 2*a*1, 2*b*1, for example. The deposition may be done using an inkjet when a small amount of compound is to be deposited, using a standard pipetting technology, or by pipetting by hand for larger amounts, for example. A typical volume of approximately 0.1 microliter of detection reactants can be deposited in the first part of the channel sections 2*a*1, 2*b*1 as shown in FIG. 8, and lyophilized. If a larger volume is required or more convenient to deposit, it can be deposited directly in the sections of the measurement channel that is also referred to as sample collection unit 13 or sample processing unit 24.

In FIG. 8, analytes 4 are referred to as ovals, detection reactants 3 are referred to as crosses, and particulates 25 are referred to as small dots.

The end of each channel section 2*a*1, 2*b*1 is connected to a microstructure 5 in the form of a filter. The microstructure 5, for example, may be composed of rectangular (as shown) or circular posts having a diameter of approximately five micrometers spaced hexagonally with a separation distance of approximately five micrometers. The posts may have approximately the same height as the channel section 2*a*1, 2*b*1. The microstructure 5 can have a length of approximately 5 mm and a width of approximately 400 micrometers similar to the channel but it can also be made larger and longer for increasing the readability of the test.

In one illustrative embodiment, the detection reactants 3 for forming the networked product 6 with the analyte 4 to be detected may be particles coated with multiple copies of a ligand for the analyte 4. In one illustrative embodiment, these particles may be made in latex or polystyrene, have a density close to that of water, contain strongly colored dyes, and may have a chemically inert surface excepted for the areas with the ligands. In one illustrative embodiment, these particles are approximately 1 micrometer in diameter so that a networked product 6 with an average diameter larger than 5 particles is retained by the microstructure 5. In this case, two or a few particles interacting with each other via non-specific interactions will not be retained by the microstructure 5. Similarly, very small networked products 6 will not be retained either.

For the detection of viruses, such as H5N1 types of viruses, the ligand on the particles may be a sugar residue for which the virus shows affinity. Hemagglutinin proteins on the viral coat of influenza viruses may be used to form a networked product with ligands on the particles. By using different types of sugar residues, the specificity of a type of virus for a host can be determined. Sugars residues can be crosslinked to the surface of the particle using standard techniques such as the ones used for the preparation of glycan arrays or for crosslinking chemicals or proteins to surfaces. The particles can be coated with several types of glycans if the detection of a broad spectrum of viruses using only one signal area is desired. Another possibility is to use antibodies or antibody fragments as ligands on the particles. Particles can also be coated with different types of antibodies. Other types of ligands on the particles can be used such as red blood cells, peptides or phages, for example.

The microstructure 5 may be followed by connecting channels 2*a*2, 2*b*2 and a capillary pump (not shown). The dimensions of the connecting channels 2*a*2 and 2*b*2 may be dimensioned such that as at least one of their dimensions (e.g., height and/or width) is smaller than the smallest dimension of the sample processing unit 24. In particular, this ensures that a stronger capillary pressure exists in the connecting channel 2*a*2, 2*b*2 than in the cavity of the sample processing unit 24 in order to move the liquid forward. The capillary pump may have a total volume equivalent to the volume of the cavity, which is approximately 100 microliters in the present example. The total volume of the capillary pump may determine the volume of liquid passing through the filter and can be used in determining the overall time needed for the test.

Flow of liquid in the capillary pump can be accelerated or slowed by increasing or decreasing the critical dimensions of the structures in the pump. In a first approximation, structures spaced further apart in a capillary pump will generate a smaller capillary force and smaller flow rate than structures spaced more closely. If structures are however, too close in a capillary pump, the hydraulic resistance will impact significantly the rate of filling of the pump. Additionally, aggregates comprising a few particles might clog a capillary pump having too narrowly spaced structures. Hexagonal structures spaced approximately 20 micrometers apart from each other and forming a hexagonal lattice may be used. The dimension and height of these structures can be varied together with the outer dimensions of the capillary pump so as to determine the total volume of the pump that can be filled with liquid.

A capillary pump can comprise areas having different volumes and generating different capillary pressures to increase or decrease the flow rate of liquid passing through the device. A capillary pump may have one or a few venting channels at its end to ensure that air can be displaced by a liquid filling the device. The venting channel can be extended by a large, open venting cavity generating a very small capillary pressure. In this case, air escapes through the venting channel and venting cavity and the liquid fills the venting channel but stops at the junction area between the venting channel and the venting cavity. An alternative is to have the venting channel and/or the venting cavity hydrophobic. If COC is used, this can be done by masking the venting channel and/or the venting cavity during coating the other areas of the device with gold.

The illustrative embodiments of the present invention are not restricted to the use of a single measurement channel and may incorporate further measurement channels such as shown by way of example in FIG. 8. In this regard, and by way of example, an illustrative embodiment of the present invention may incorporate a further measurement channel, hereinafter being referred to as the second measurement channel 2b. Properties of the second measurement channel 2b, which has an associated microstructure, may be chosen to differ from that of the first measurement channel 2a, thereby to obtain a further insight into the sample and/or analyte detected in the sample. For example, the second measurement channel 2b may be configured to differ from the first measurement channel 2a in that it has at least a different associated hydrodynamic and/or chemical property.

Regarding the difference in hydrodynamic properties, different levels of sensitivity may be incorporated in illustrative embodiments of the present invention. For example, the capillary pumping of the first measurement channel 2a may be chosen to be slower than the second measurement channel 2b. Thus, a higher sensitivity yield may be obtained from the results associated with the first measurement channel 2a relative to the second measurement channel 2b. The second or further measurement channels in illustrative embodiments of the present invention may each also be configured to have an associated chemical property that is different from that of the first measurement channel 2a. For example, the inner walls of the second measurement channel 2b may be adapted for the further reduced probability of adhesion of the sample and/or detection reactant 3 thereto, compared to the first measurement channel 2a. In this way, the performance of illustrative embodiments of the present invention may be further improved by virtue of the increased probability of interaction between the sample and the detection reactant 3 and the decreased probability of clogging of the measurement channel.

In some illustrative embodiments of the present invention, the second measurement channel 2b may be configured to differ from the first measurement channel 2a such that the networked product 6 is formed with a different characteristic. By way of example, the second measurement channel 2b may be configured to comprise the same detection reactant 3 as that in the first measurement channel 2a. Thus, they will detect the same analyte 4, if it is present in the sample. By configuring the second measurement channel 2b such that the networked product 6 is formed with a different formation characteristic compared to that in the first measurement channel 2a, the concentration of the analyte 4 may be determined.

In this regard, and for the sake of example, the formation characteristic may be chosen to be the length of the measurement channel. In this regard, the second measurement channel 2b may be configured such that the interaction of the sample with the detection reactant 3 to form the networked product 6 and the collection of the networked product 6 by the microstructure associated with the second measurement channel 2b occurs over a shorter length than in the first measurement channel 2a. For substantially the same characteristics being possessed by the microstructures associated with the first and second measurement channels 2a and 2b, the concentration of the networked product 6 collected by the microstructure associated with the second measurement channel 2b will be necessarily higher than that collected at the first measurement channel 2a. Obtaining knowledge on the concentration of the analyte 4 in a sample may be advantageously applied to determine the treatment to be administered to a person. Furthermore, by applying an illustrative embodiment of the present invention to determine the concentration of an analyte 4 periodically, monitoring the effect of administered drugs and an incubation period of viruses, for example, may be done.

In some illustrative embodiments of the present invention, the second measurement channel 2b may be configured to differ from the first measurement channel 2a in that it comprises a different detection reactant 3. In this way, the application of the illustrative embodiments of the present invention may be extended for the simultaneous detection of a further analyte, if it is present in the sample. In this case, the sample may also be flowed in the second measurement channel 2b in which a detection reactant 3 corresponding to the further analyte is stored. The networked product 6 formed by the interaction of the further analyte in the sample and the detection reactant 3 in the second measurement channel 2b may be collected by a microstructure 5 that is associated with and coupled to the second measurement channel 2b. This provides the advantage that illustrative embodiments of the present invention being able to be configured, for example, to detect the different influenza viruses, A and B, simultaneously.

To provide ease of sample collection, a sample collection unit 14 may be provided that comprises a swab, in some illustrative embodiments of the present invention, this feature being most clearly seen from FIG. 5. FIG. 5 refers to an illustrative embodiment of the present invention showing an apparatus 1 comprising an elongated housing 21 inside which the measurement channel 2a is formed, and at the end of which the sample collection unit 14 is attached. The sample collection unit 14 may be prepared with chemicals added thereto so that processing of the sample can be initialized.

Typically, a given measurement channel 2a in an illustrative embodiment of the present invention is a microfluidic capillary and has dimensions on the micron-scale. Thus, this may pose a challenge to visually detect the filtered networked product 6. In order to alleviate this problem, a viewing zone 15 is provided in some illustrative embodiments of the present invention, which is configured to enhance the visual detection of the filtered networked product 6, this feature being most clearly seen in FIG. 5. In one illustrative embodiment, the viewing zone 15 is a window provided above the region where a microstructure 5 corresponding to the first and/or second measurement channel is coupled thereto. In one illustrative embodiment, the window comprises a material that is substantially transparent and/or that comprises a magnifier.

With reference being made to FIG. 6, one illustrative embodiment of an apparatus according to FIG. 5 is shown schematically with a cover 22 of the housing 21 being detached from a base 23 of the housing 21.

The housing 21 may be made in a plastic material, which can be embossed at elevated temperature or mold injected. A material such as polymethyl methacrylate, polystyrene, cyclic olefin copolymer (COC), or the like, can be used. COC may be preferred in some cases because it is a mechanically and chemically resistant plastic, it is highly non-permeable to water, and it is well transparent to visible and ultraviolet light. The housing 21 may be formed by assembling two matching parts, such as the base 23 and the cover 21, as shown in FIG. 5. The detection reactants 3 may be added in one part or both parts of the housing 21. In one illustrative embodiment, the base 23 is molded to define the finest microfluidic structures that are needed for a test while the cover 21 has an optically transparent window 15a in the region where the networked product 6 is collected. For example, the microstructure 6 for filtering the networked product 6 is molded in the base 23 in order to prevent having to precisely combine two parts to form an entire microstructure 5. Any structures in the base 23 may have all the same depth to simplify the fabrication of a high precision mold because it can be difficult to prepare molds that have small and large features with different heights.

In order to generate a capillary pressure that can displace a liquid from, for example, a pad or the swab as shown in FIGS. 5 and 6 where the sample is loaded by the user to the capillary pump, the surfaces in the apparatus, and more specifically the inner surfaces of the housing 21, may be wettable. Plastic surfaces can be made wettable using a brief exposure to a oxygen-based plasma or exposure to ozone produced using deep ultraviolet light and oxygen, for example. Another possibility is to coat the inner surface of the base 23 of the housing 21 with titanium and gold. In one illustrative embodiment, a method is used to deposit approximately 2 nm of titanium and approximately 10 nm of gold using a sputtering method. The titanium layer acts as an adhesion promoter between the plastic and the gold and thereby ensures strong adhesion of the gold to the plastic material. The inner surface of the cover can be left free of gold to ensure a good transparency of the material in the region where the indicator should be seen. Alternatively, gold can be sputtered selectively in some areas of the inner surface of the cover by using a stencil mask or a shadowed evaporation. Freshly deposited gold is hydrophilic and can be covered with a layer of alkanethiols. Gold may be covered with poly(ethylene glycol)-functionalized alkanethiols to make the gold surface hydrophilic as well as protein-repellent.

The apparatus 1 according to FIG. 6 may further comprise a sample collection channel 11 that is configured to be unidirectionally coupled to a sample storage unit 12. In this case, excess sample may be channelled into the sample collection channel 11 and then directed to the sample storage unit 12 where it is stored. The sample collection channel 11 is configured such that the flow of the sample is unidirectional, i.e. in the direction of the sample storage unit, and unable to revert on its flow path. By excess sample, what is meant is any sample volume that remains after flowing of the sample in the measurement channel(s). The sample collected in the sample storage unit 12 may be applied for further testing. In this case, the sample storage unit 12 may be detached and capped for suitability of transportation off-site for further testing. Alternatively, an embodiment of the present invention may be capped and transported for further investigations to be conducted.

As can be seen from FIG. 6, the sample collection unit 43 may be configured for the collection of the sample to be tested. A sample to be tested for the presence of a particular analyte may be collected from a person/animal via the sample collection unit 14, which is then appended to one or more of the measurement channels 2a, 2b, in an illustrative embodiment of the present invention. The sample collection unit 14 further comprises at least a sample processing unit (not shown). By way of this feature, pre-processing of the sample may be done, for example, to alter its physical properties thereby to improve the performance of an illustrative embodiment of the present invention in the detection of a given analyte 4. Such physical properties may include pH, viscosity, transparency, stability and ionic-strength, for example. In this regard, the sample collection unit 14 may be configured to comprise at least a filter (not shown). By incorporating a filter in the sample collection unit 14, it becomes possible to reduce the probability of mucus, tissue fragments, cells, etc present in the sample collected from a person/animal to be tested from entering and/or clogging the flow path of the sample in the measurement channel 2a. In this way, the performance of an illustrative embodiment of the present invention may be further improved.

The visual detection of the networked product 6, collected in the microstructure 5 coupled to a given measurement channel, is dependent on the concentration of the networked product 6 that is formed. In order to compensate for the reduced visibility of the networked product 6 collected by the microstructure 5, if it is formed with a reduced concentration, the measurement channel 2a, 2b may be designed to have a predefined geometrical shape 18 in the region where it is coupled to its associated microstructure 5. In this regard, and in some illustrative embodiments of the present invention, the geometrical shape is chosen so as to enhance the visual detection of the networked product 6 collected by the microstructure 5. For example, the measurement channel 2a, 2b, may incorporate a step where it is coupled to its associated microstructure. This is shown by way of an example in FIG. 7, The visibility zone 15 enables the user to monitor the microstructures 5 of three channels 2a, 2b, 2c. Each microstructure is implemented in a portion of the respective channel which is designed as a step in the channel. Instead of widening the channel structure of each channel in an area where the microstructure sits in order to improve visibility for the user, a more scale efficient way is to implement the microstructure in vertical portions of the channel and as such preventing from widening the entire apparatus. This stepped geometry increases readability of the test by using better the space available across the width of the apparatus. This feature may also be applied in incorporating the desired number of measurement channels without the need to change the form factor of the illustrative embodiments of the present invention. For example, fewer but wider measurement channels may be implemented or, alternatively, more but narrower-width measurement channels may be incorporated in illustrative embodiments of the present invention, which would both serve to enhance the visual detection of the networked product 6 collected in the microstructures 5 associated with the measurement channels.

Features that have been described with reference to the first measurement channel 2a are not restricted thereto and may also be applied to the second or further measurement channels of the present invention.

The present invention has been described above purely by way of example and modifications of details can be made within the scope of the invention. Each feature disclosed in the description, and where appropriate, the claims and drawings, may be provided independently or in any appropriate combination.

The invention claimed is:

1. An apparatus for the detection of an analyte in a sample comprising:
at least a first measurement channel comprising a detection reactant corresponding to the analyte to be detected; and
at least a microstructure associated with the first measurement channel, wherein:
when the apparatus is in use, the sample is introduced into the first measurement channel and propagated by way of the first measurement channel towards the microstructure such that the analyte, if it is present in the sample, interacts with the detection reactant to form a networked product,
the microstructure is configured to filter the networked product such that the networked product is collected by the microstructure and non-networked particles of the sample pass through the microstructure, further comprising at least a second measurement channel with at least an associated second microstructure, wherein the first measurement channel and second measurement channel are separate from one another and are both connected to a same sample processing unit of the apparatus such that a first portion of the sample flows from the sample processing unit into the first measurement channel and a second portion of the sample separately flows from the sample processing unit into the second measurement channel, and
the first measurement channel has a different length than the second measurement channel, such that different concentrations of the analyte are detected by the first measurement channel and the second measurement channel.

2. The apparatus as claimed in claim 1, wherein the second measurement channel is configured to differ from the first measurement channel in that it has at least one of a different associated hydrodynamic property or different associated chemical property from the first measurement channel.

3. The apparatus as claimed in claim 1, comprising at least one of a third microstructure associated with the at least one of the first measurement channel or a fourth microstructure associated with the at least one second measurement channel, the third microstructure having a different physical configuration from the first microstructure so as to filter networked products having at least one of a different minimum size or different shape than network products filtered by the first microstructure, and the fourth microstructure having a different physical configuration from the second microstructure so as to filter networked products having at least one of a different minimum size or different shape than network products filtered by the second microstructure.

4. The apparatus as claimed in claim 1, wherein at least one of the first or second measurement channel is configured to further comprise at least an inhibitor, wherein the inhibitor operates to either control a size of the networked product, reduce a probability of coagulation of particles, or inhibit interaction of the detection reactant with other known analytes.

5. An apparatus for the detection of an analyte in a sample comprising:
at least a first measurement channel comprising a detection reactant corresponding to the analyte to be detected; and
at least a microstructure associated with the first measurement channel, wherein:
when the apparatus is in use, the sample is introduced into the first measurement channel and propagated by way of the first measurement channel towards the microstructure such that the analyte, if it is present in the sample, interacts with the detection reactant to form a networked product, and
the microstructure is configured to filter the networked product such that the networked product is collected by the microstructure and non-networked particles of the sample pass through the microstructure, wherein the microstructure comprises a plurality of posts having approximately a same height as the first measurement channel.

6. The apparatus of claim 5, wherein each of the posts in the plurality of posts has a rectangular or circular size of approximately 5 micrometers in diameter.

7. The apparatus of claim 5, wherein the posts in the plurality of posts are spaced hexagonally relative to one another with a separate distance of approximately five micrometers.

8. An apparatus for the detection of an analyte in a sample comprising:
at least a first measurement channel comprising a detection reactant corresponding to the analyte to be detected; and
at least a microstructure associated with the first measurement channel, wherein:
when the apparatus is in use, the sample is introduced into the first measurement channel and propagated by way of the first measurement channel towards the microstructure such that the analyte, if it is present in the sample, interacts with the detection reactant to form a networked product, and
the microstructure is configured to filter the networked product such that the networked product is collected by the microstructure and non-networked particles of the sample pass through the microstructure, wherein the microstructure has a length of approximately 5 mm and a width of approximately 400 micrometers.

9. The apparatus of claim 1, wherein the first measurement channel has a different capillary pumping characteristic than the second measurement channel such that a flow of the first portion of the sample through the first measurement channel is slower than a flow of the second portion of the sample through the second measurement channel.

10. The apparatus of claim 1, wherein walls of the first measurement channel are adapted to reduce probability of adhesion of the sample compared to walls of the second measurement channel.

11. The apparatus of claim 1, wherein the first measurement channel is configured to detect a first analyte in the sample and the second measurement channel is configured to detect a second analyte in the sample.

* * * * *